(12) United States Patent
Domard et al.

(10) Patent No.: US 9,044,410 B2
(45) Date of Patent: Jun. 2, 2015

(54) FILAMENT BASED ON HYALURONIC ACID IN THE FORM OF FREE ACID AND METHOD FOR OBTAINING IT

(71) Applicants: UNIVERSITE CLAUDE BERNARD LYON I, Villeurbanne Cedex (FR); CENTRE NATIONAL DE LA RECHERCHE SCIENTIFIQUE, Paris Cedex (FR)

(72) Inventors: Alain Domard, Lyons (FR); Laurent David, Lyons (FR); Florence Dupasquier, Paray le Monia (FR)

(73) Assignees: UNIVERSITE CLAUDE BERNARD LYON I, Villeurbanne (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/269,315

(22) Filed: May 5, 2014

(65) Prior Publication Data
US 2014/0242146 A1    Aug. 28, 2014

Related U.S. Application Data

(62) Division of application No. 12/680,257, filed as application No. PCT/FR2008/051729 on Sep. 26, 2008, now Pat. No. 8,753,671.

(30) Foreign Application Priority Data

Sep. 28, 2007 (FR) ..................................... 07 57957

(51) Int. Cl.
| | | |
|---|---|---|
| *A61K 9/70* | (2006.01) | |
| *A61F 13/00* | (2006.01) | |
| *D02G 3/00* | (2006.01) | |
| *D01D 5/06* | (2006.01) | |
| *D01F 9/00* | (2006.01) | |
| *D01F 11/00* | (2006.01) | |
| *A61K 47/36* | (2006.01) | |
| *A61L 27/20* | (2006.01) | |
| *C08J 7/04* | (2006.01) | |
| *C08J 7/06* | (2006.01) | |

(52) U.S. Cl.
CPC ............... *A61K 9/70* (2013.01); *Y10T 428/298* (2015.01); *Y10T 428/2913* (2015.01); *Y10T 428/2933* (2015.01); *D01D 5/06* (2013.01); *D01F 9/00* (2013.01); *D01F 11/00* (2013.01); *A61K 47/36* (2013.01); *A61L 27/20* (2013.01); *C08J 7/04* (2013.01); *C08J 7/065* (2013.01); *C08J 2305/08* (2013.01)

(58) Field of Classification Search
CPC .. A61K 2300/00; A61K 8/735; A61K 31/728
See application file for complete search history.

(56) References Cited

U.S. PATENT DOCUMENTS

| | | | |
|---|---|---|---|
| 5,527,337 A | 6/1996 | Stack et al. | |
| 6,099,952 A * | 8/2000 | Cercone | ..................... 428/308.4 |
| 6,592,794 B1 | 7/2003 | Bachrach | |
| 2004/0224406 A1* | 11/2004 | Altman et al. | ................ 435/395 |
| 2005/0073075 A1 | 4/2005 | Chu et al. | |
| 2006/0046590 A1 | 3/2006 | Chu et al. | |

FOREIGN PATENT DOCUMENTS

WO       97/30093 A1    8/1997

OTHER PUBLICATIONS

A. Rupprecht: Wet Spinning of Hyaluronic Acid, Preparation of Oriented Samples, vol. B33, No. 10, 1979, pp. 779-780, Department of Physical Chemistry, Arrhenius Laboratory, University of Stockholm, Stockholm, Sweden.
I. C. Um, et al.: Electro-Spinning and Electro-Blowing of Hyaluronic Acid, Biomacromolecules, vol. 5, Jul. 5, 2004, American Chemical Society, pp. 1428-1436.
Hirano et al. Carbohydrate Polymers, 2000, 43, 281-284.
Keenan, Applied Microbiology, 1968, 1881-1885.
Ruan et al. Macromol. Biosci., 2004, 4, 1105-1112.
Tamura et al. Materials Science and Engineering C, 2002, 20, 143-147.
Um et al. International Journal of Biological Macromolecules, 2004, 34, 107-119.

* cited by examiner

*Primary Examiner* — Gina Justice
*Assistant Examiner* — Genevieve S Alley
(74) *Attorney, Agent, or Firm* — Kenyon & Kenyon LLP

(57) ABSTRACT

The present invention relates to a method for preparing by wet spinning a continuous filament based on hyaluronic acid in free acid form, notably soluble in water. The preparation method according to the invention comprises the following steps: a) preparing a spinnable aqueous solution of hyaluronic acid or of a hyaluronic acid salt, preferably a sodium hyaluronate solution; b) extruding said solution to an extrusion die; c) forming the filament by passing the extruded solution into a bath of acetic acid, concentrated to more than 80%, drawing and drying. The invention also relates to a filament based on hyaluronic acid in free acid form, said filament having swelling properties in water and physiological liquids and moreover being solubilizable in water under certain conditions.

19 Claims, 2 Drawing Sheets

FILAMENT BASED ON HYALURONIC ACID IN THE FORM OF FREE ACID AND METHOD FOR OBTAINING IT

CROSS REFERENCE TO RELATED APPLICATIONS

This application is a divisional of U.S. patent application Ser. No. 12/680,257, filed May 10, 2010, which is a 371 national phase application of PCT/FR2008/051729 filed Sep. 26, 2008, claiming priority to French Patent Application No. 0757957 filed Sep. 28, 2007, the contents of which are incorporated herein by reference.

FIELD OF THE INVENTION

The present invention relates to the field of biomaterials and its object is a method for preparing by wet spinning a filament based on hyaluronic acid, notably soluble in water. The invention also relates to a filament based on hyaluronic acid, said filament having swelling properties in water and physiological liquids and moreover being able to be solubilized in water under certain conditions. The invention also relates to the use of the thereby obtained filament based on hyaluronic acid for elaborating various biomaterials.

BACKGROUND OF THE INVENTION

Hyaluronic acid is a major constituent of connective tissues. It was discovered in bovine vitreous humor in 1934 by Karl Meyer [2] but its chemical structure was only able to be determined in the 1950ies [3, 4] (numerical references between square brackets relate to bibliographic references appearing at the end of the description).

It is mainly found in the epidermis (2-4 mg/mL), the dermis (~0.5 mg/mL), the umbilical cord (~4 mg/mL), the vitreous humor and in synovial liquid.

Hyaluronic acid is a polyelectrolyte, i.e. a polymer bearing ionizable groups capable of being dissociated in polar solvents, in order to form a charged polymer chain surrounded by more or less mobile counter-ions. The presence of charges gives to polyelectrolytic solutions remarkable physicochemical properties corresponding to many applications.

Polyelectrolytes are used for their flow properties as thickeners or gelling agents, in cosmetics notably [1]. They are also used for their properties of adsorption to interfaces.

Further, they are widely present in biological media, which recommends their use within the scope of biomedical devices.

Because of its viscoelastic properties giving it great lubricating power, hyaluronic acid is used for viscosupplementation [5], the injection of hyaluronic acid in the joints having the goal of restoring homeostasia of synovial liquid by improving its flow properties and by promoting endogenous production of hyaluronic acid.

The properties of hyaluronic acid have also been exploited in ophthalmology [6]. It is used as a gel, as a protective agent of eye cells upon contact with surgical instruments and implants, during eye microsurgery operations. The main formulations of HA marketed for this type of applications are Healon® (Advanced Medical Optics, USA), Opegan® and OpeganHi® (Santen Pharmaceuticals, Japan).

With its great power for retaining water, hyaluronic acid plays a primordial role in moisturizing skin. It acts with collagen in order to give the cells some rigidity contributing to the flexibility of skin and, by being associated with proteoglycans of the skin, hyaluronic acid forms a network capable of preventing the passage of macromolecules (often toxic) and of facilitating that of small electrolytes in water.

For all these reasons, hyaluronic acid is used in the cosmetic field for formulating creams or gels.

A method for wet spinning of hyaluronic acid was developed in the years 1960-1970 for allowing the preparation of hyaluronic acid films having an oriented structure [7,8,9]. The method is the adaptation of a procedure and of a device developed for preparing DNA samples. In the wet spinning method described in document 9, a solution of potassium hyaluronate (2.5 to 3 mg/mL in a 0.1M KCl solution) is continuously extruded through a die including 720 cylindrical channels each having a diameter of 70 µm and a length of 1.5 mm. The potassium hyaluronate solution is extruded in a bath containing 75-80% ethyl alcohol in 0.1M KCl. The potassium hyaluronate fibers precipitate and are then grouped in a bundle and wound on a rotary cylinder. Said fibers are then dried which leads to the formation of a film by coalescence.

Short fibers (nanofibers) of hyaluronic acid, grouped as membranes, have also been obtained by the electro-spinning and blowing-assisted electro-spinning technique [10,11].

With the mentioned methods, it is not possible to obtain hyaluronic acid filaments but only membranes consisting of networks of nanofibers, i.e. fibers of very short length.

Moreover, materials based on hyaluronic fibers were able to be obtained by cross-linking of hyaluronic acid in the presence of cross-linking agents of the carbodiimide or epoxide type (cross-linking agents, a non-exhaustive list of which is for example mentioned in document US 2007066816). These materials however have the non-negligible disadvantage of being toxic for humans, which severely limits their interest in all uses in vivo. Further, these materials are insoluble in water.

SUMMARY OF THE INVENTION

The present invention proposes to overcome the aforementioned drawbacks exhibited by known materials based on hyaluronic acid.

Its first goal is to provide a novel method for making a material based on hyaluronic acid appearing as a continuous filament which is free of chemical cross-linking agent.

The term of <<filament>> is defined in the sense of the invention as a continuous unit fiber of very great length, normally not being interrupted during its manufacturing process, the length of said filament being measured in meters or at least in tens of centimeters.

According to a first aspect, the invention relates to a method for preparing by wet spinning a filament based on hyaluronic acid in free (or protonated) acid form, said method being characterized in that it comprises the following steps:
a) preparing a spinnable aqueous solution of hyaluronic acid or of a salt of hyaluronic acid, preferably a sodium hyaluronate solution;
b) extruding said solution through an extrusion die;
c) forming the filament by passing the extruded solution in a bath of concentrated acetic acid, the concentration of which is sufficiently high in order to obtain coagulation of the extruded solution as a coagulated filament, drawing and drying.

By the expression of <<spinnable solution>>, is meant a solution, for which the notably flow characteristics make it continuously extrudable.

The formation of the filament is accomplished by coagulation. The solution of hyaluronic acid or of the salt of hyaluronic acid, which is extruded through the die, is gradually set in its bulk upon passing into the coagulation bath, the coagulating agent of which is the concentrated acetic acid solution. For example, acetic acid is concentrated to more than 80%, preferably to more than 90%. At this concentration, hyaluronic acid is no longer soluble. Thus by diffusing the acetic acid solution into the extruded solution, it is possible to have the hyaluronic acid pass from the liquid state to a physical hydrogel state, in the form of a hyaluronic acid/acetic acid complex, until a continuous filament is obtained, the section of which is completely coagulated, drawing and drying giving said filament its mechanical characteristics making it easy to handle. In the case when the extruded solution is a solution of a salt of hyaluronic acid, acetic acid causes its hydrolysis into hyaluronic acid on the one hand and on the other hand into an acetate, which is soluble in the concentrated acetic acid solution; consequently, a physical hydrogel is obtained in the same way, whether one starts with a hyaluronic acid solution or a hyaluronic acid salt solution, in the form of a hyaluronic acid complex in the free acid/acetic acid form.

Preferably, the spinnable solution is at a concentration of at least 0.8% by weight of hyaluronic acid or the weight equivalent of the hyaluronic acid salt. Below this concentration, the viscosity of the solution is insufficient for allowing continuous extrusion. Advantageously, it is at a concentration of the order of 1-2% by weight of hyaluronic acid. Of course, the concentration may vary depending on the diameter of the die used.

Preferably, the preparation of the spinnable solution consists of dissolving in water a determined amount of sodium hyaluronate in order to obtain the intended concentration, and of performing degassing of the obtained solution, this in order to remove the dissolved gases which may generate bubbles during the formation of the filament.

The drawing ratio may be small, for example from 1.05-1.10, in this case achieved on the coagulated filament, during the drying, in order to exert sufficient tensioning of said filament in order to maintain its geometry and avoid any deformation during its travel until it is wound.

However, it is preferable to exert drawing at a larger ratio, for example of 2 or even more, under conditions allowing this drawing to occur mainly on the extruded spinnable solution between the die outlet and the coagulation bath. This drawing, possible because of the excellent viscoelastic properties of notably sodium hyaluronate solutions, allows adjustment of the diameter of the filament and of its mechanical properties.

The drying is generally total drying, so as to obtain a filament which is exclusively formed of hyaluronic acid in the form of free acid and with a small proportion of water, of the order of 8-12% by weight when it is conditioned in a normal atmosphere. More intense drying would destroy the hyaluronic acid/acetic acid/water complex by removing the acetic acid and water. Nevertheless, drying may optionally be partial, either for obtaining a filament free of acetic acid but having a greater proportion of water, or for obtaining a filament retaining a certain proportion of acetic acid within the scope of applications in which the presence of this component is not redhibitory.

It should be noted that the 8-12% water content is the usual water content of a polysaccharide such as hyaluronic acid in the dry condition when the latter is in a non-ionized form, and in the present case, in the form of free acid. Conversely, any polysaccharide in the ionized form, notably as a salt, contains under the same conditions, 16-18% water. The low water content of the hyaluronic acid filament in free acid form has significant consequences on its notably mechanical properties.

The filament directly obtained by the aforementioned method may hydrate and therefore swell upon contact with water or physiological media; it remains soluble in water under conditions which are notably function of its crystallinity and therefore on the drawing ratio to which it was subject.

It may however be desirable to reduce its reactivity to water. To do this, according to an alternative embodiment, the step for forming the hyaluronic acid filament in the free acid form is followed by a step for coating said filament with a compound capable of slowing down its hydration, and therefore swelling and solubilizing of the filament in water or in a physiological medium. The coating compound remains at the surface and does not diffuse in depth into the filament. Coating is accomplished by passing the filament in a coating bath, for example containing from 0.10-10% by weight of the coating compound.

Said coating compound in one embodiment, is a natural macromolecule such as chitosan or collagen. As these natural polymers bear ionic sites, electrostatic interaction occurs with hyaluronic acid of the polyanion/polycation type, which increases the interaction between the coating compound and the filament. Further, in this case like moreover in that of a coating based on polymer not having any ionic charges, hydrogen bonds and hydrophobic interactions develop.

In another embodiment, the coating compound of the filament is a fatty compound of vegetable or animal origin, for example vegetable wax deposited in the molten state.

It may also be interesting to include in the interfibrillar spaces of the filament, active ingredients, which may then be subsequently salted out when the filament is in contact with a liquid medium, notably a physiological medium. This inclusion is obtained by plunging the filament in an impregnation bath containing said active ingredients, the porosity of the filament allowing their diffusion towards the inside of the filament into the interfibrillar spaces, and then by drying the thereby impregnated filament. Under the expression of <<active ingredients>>, are designated all molecules of biological interest in the field of biotechnologies, among which hormones, grow factors, interleukins, interferons, antibacterial agents, antifungal agents and biostimulating agents. The salting-out rate of the active ingredient depends on the interaction between said ingredient and the filament. Salting-out is relatively fast if there is no interaction. However if there are interactions, salting-out may either be controlled via a physico-chemical route, or by gradual biodegradation of the filament, in particular in the latter case if the interactions are very strong.

The object of the invention is also a filament based on hyaluronic acid in free acid form capable of being obtained by the aforementioned method. In a characteristic way, the basic filament, which is free of chemical cross-linking agents, only contains hyaluronic acid in free acid form and water. It should be noted that the residual salt, notably the sodium acetate form during the aforementioned method, is solubilized in the concentrated acetic acid solution and is therefore not in the filament. The absence of cross-linking agent guarantees better biocompatibility since said agents have some toxicity and therefore induce inflammatory reactions in vivo.

The filaments of the invention in the dry condition have a water content from 8-12%. They have interesting swelling properties under physiological conditions. This makes them very good candidates for filling wrinkles.

The object of the invention is also a coated filament based on hyaluronic acid which comprises at its surface a coating of a compound which may reduce its hydration, for example chitosan or collagen or a fat of animal or vegetable origin, notably a wax of vegetable origin.

The object of the invention is also a filament based on hyaluronic acid in free acid form which contains active ingredients included in its interfibrillar spaces.

The invention also relates to the use of the filament based on hyaluronic acid in free acid form in cosmetics, notably for filling wrinkles.

Another aspect relates to the use of a filament based on hyaluronic acid in free acid form of the invention for elaborating textile materials, for example non-woven materials, for making healing bandages.

BRIEF DESCRIPTION OF THE DRAWINGS

Other characteristics and advantages of the invention will become apparent upon reading the detailed description and exemplary embodiments which will follow, as well as appended figures wherein.

DETAILED DESCRIPTION

Figure 1:
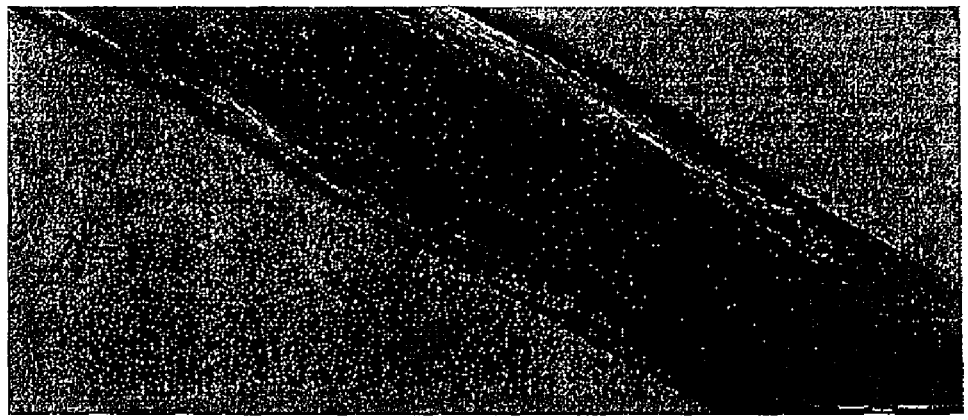
FIG. 1 illustrates the hyaluronic acid filament in free acid form according to the invention as seen with an optical microscope.

The present invention relates to a method for preparing by wet spinning a continuous filament based on hyaluronic acid in free or protonic acid form, from a spinnable aqueous solution of hyaluronic acid or of a salt of hyaluronic acid, preferably sodium hyaluronate.

In the present description, the expression of <<hyaluronic acid>> should be understood as designating hyaluronic acid in the free or protonated acid form.

In order to prepare the spinnable solution, a sufficient amount of sodium hyaluronate is dissolved in water in order to obtain a viscous solution capable of being spun by itself, without dripping. It is noted that below 0.8% by weight, the solutions are not sufficiently viscous. For concentrations of the order of 1-2%, the solutions have viscoelasticity such that they spin with the spatula. Of course, the sodium hyaluronic concentration is selected depending on the diameter of the extrusion die. Within an experimental framework, when the extrusion die is a thin needle, the diameter of which is of the order of 0.8 mm, too great viscosities prevent the passing of the solution through the die, in which case, in the examples below, solutions with 1% by weight of sodium hyaluronate were preferred.

In order to avoid problems of rupture and so that it is spinnable under good conditions, the solution used is subject to a degassing step; indeed, the gases dissolved in the solution form small bubbles which may be at the origin of embrittlement of the filament. Degassing is all the more significant and difficult since the solutions are viscous.

The thereby prepared spinnable solution is extruded through an extrusion die, immersed in a coagulation bath containing a coagulating agent, drawn and dried, and the obtained filament is received. The extrusion conditions, notably the extrusion rate, should allow the formation of a coagulated filament of constant diameter. The coagulation bath is a concentrated solution of acetic acid. The concentration of this acetic acid is sufficiently high in order to obtain gradual diffusion into the extruded solution of hyaluronic acid with which hyaluronic acid may pass from the liquid state to the physical hydrogel state, no doubt as a hyaluronic acid/acetic acid/water complex, until a filament is obtained, the cross-section of which is completely coagulated. This is acetic acid at a concentration of more than 80%, preferably more than 90%.

Within an experimental framework, the extrusion was accomplished by applying a syringe equipped with a syringe pump RAZEL R-99E and with a needle acting as an extrusion die, with a diameter of the order of 0.8 mm. The extrusion rate was between 1.2 and 15 cm/min.

Duration of the coagulation is controlled in three ways: by the running speed of the filament in the bath in the one hand, by the volume of solution contained in the reactor containing the coagulation bath on the other hand, and finally by the path covered by the filament inside this reactor. The dwelling time should be sufficient so that the filament is completely coagulated.

Drawing is achieved by means of a rotary motorized system which pulls the filament at a greater rate than the extrusion rate and which receives it optionally. The drawing ratio is the ratio between the rate in linear meters of said rotary system and the extrusion rate in linear meters. The drawing may occur on the coagulated filament; in this case, the drawing ratio is not very large, of the order of a few percent, mainly having the purpose of maintaining the geometry of the yarn during its displacement up to its reception. The drawing may occur immediately at the outlet of the die on the extruded, still not coagulated, solution and optionally partly on the extruded solution while it is being coagulated; in this case, the drawing ratio is much greater, it may be of the order of 2 or even greater than 2, this drawing mainly having the purpose of adjusting the diameter of the filament and its mechanical properties.

The drying, by any suitable means, has the purpose of removing the excess coagulation bath and reducing the proportion of acetic acid and water in the filament. During total drying, acetic acid is totally removed and the obtained filament only contains hyaluronic acid and water, with a water content from 8 to 12%.

The mechanical characteristics of the obtained filament depend on drying conditions and on the drawing ratio. In particular, the crystallinity rate of the filament changes over time like the drawing ratio.

The filament, which only contains hyaluronic acid and water, may hydrate upon contacting water or physiological solutions, with subsequent swelling. It remains soluble in water, under variable conditions depending on its manufacturing parameters.

According to an alternative embodiment, in order to make it less sensitive to hydration, the hyaluronic acid filament undergoes an additional coating step with a compound capable of slowing down hydration, and therefore swelling and solubilization of the filament, in water or in a physiological medium such as: blood, lymphatic or lachrymal liquid, etc. Said coating compound in one embodiment is a natural macromolecule such as chitosan or collagen. In another embodiment, the coating component of the hyaluronic acid filament is a fatty compound of vegetable or animal origin.

According to a second aspect, the invention relates to a continuous filament based on hyaluronic acid which may be obtained by the aforementioned method. Known hyaluronic acid fibers obtained by electro-spinning according to WEB observations have diameters of less than 50 nm. The filament according to the present invention, obtained with the aforementioned method, has a diameter which will generally range from a hundred to several hundred micrometers. Further, it has a length which is not limited, which may be of several meters or at least of several tens of centimeters.

In a characteristic way, the filament based on hyaluronic acid of the invention is free of any chemical cross-linking agent which makes it particularly suitable for uses in vivo in humans. It contains hyaluronic acid, water and possibly acetic acid. Preferably, it exclusively contains hyaluronic acid and water, notably in the dry condition with water content from 8 to 12%.

It swells in water and in a given physiological medium. Further it is capable of dissolving in water. This dissolution in water of the hyaluronic acid filament is not immediate; it is obtained by increasing the pH. Indeed, hyaluronic acid in the free or protonated acid form, i.e. non-ionized, is not directly soluble in water. A sufficient number of carboxylic sites thus have to be ionized in order to obtain perfect solubilization.

The hyaluronic acid filament was characterized by observation under the optical microscope and under the scanning electron microscope, by tensile tests as well as X-ray diffraction, as shown hereafter.

1. Determination of the Diameter of the Filaments.

The average diameter of the filaments was determined for each spinning rate with an optical microscope from four measurements conducted in different locations over the length of the same filament. It is found that spinning rate has no influence on the diameter of the filaments.

The measured diameters are comprised between 12 and 170 μm. However, the diameter of the yarns may vary by changing the drawing ratio and the diameter of the die.

The image of a filament according to the invention as viewed with an optical microscope, is illustrated in FIG. 1. This is a hyaluronic acid filament obtained from a solution of 1% by weight of sodium hyaluronate for a spinning rate of 5.9 cm/min.

2. Scanning Electron Microscopy

Figure 2:
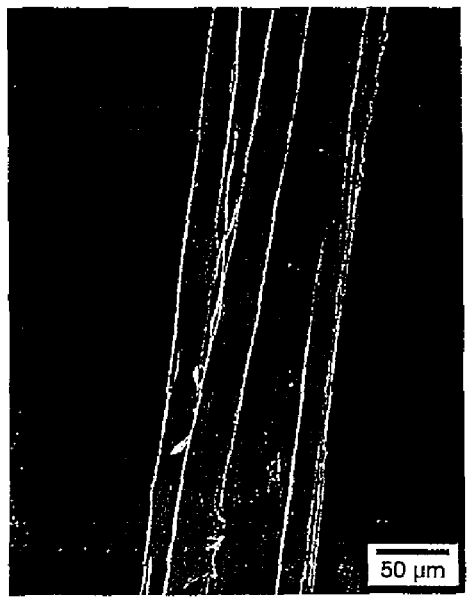
FIG. 2 shows the structure of the filament according to the invention as observed with a scanning electron microscope.
Figure 2:
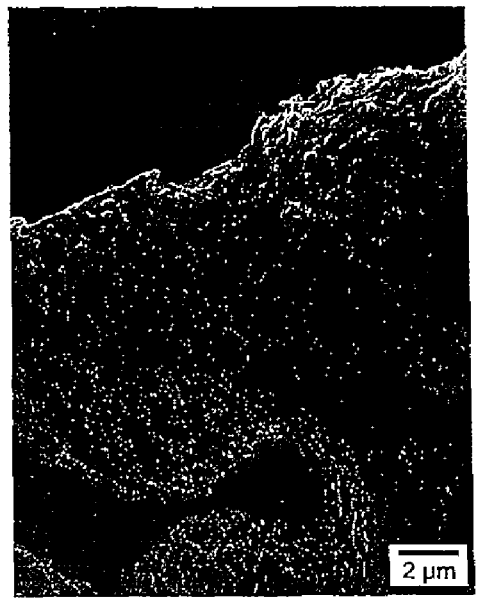

The surface condition and failure profile of filaments of hyaluronic acid were observed with a scanning electron microscope Hitachi S800 at 15 kV after metallization with gold-palladium. Failure of the filaments was achieved by immersion in liquid nitrogen from a filament wound around a needle. The images obtained from a not very highly drawn filament of hyaluronic acid, obtained from a 1% by weight solution of sodium hyaluronate, are illustrated in FIG. 2.

The filament at first sight seems to consist of several assembled fibers (FIG. 2*a*) but the failure surface (FIG. 2*b*) clearly shows that the surface relief is due to folds. These folds or villosities very certainly appear during the drying step. In FIG. 2*b*, smaller objects such as fibrils which seem to align along the axis of the filament are also observed in these villosities. Such <<nanofibrils>> have already been observed for chitosan fibers [12].

3. Mechanical Properties

Tensile tests were carried out with a tensile testing machine Adamel-Lhomargy DY22 equipped with a 10N sensor and a specific system for the yarns. Samples were prepared from a solution of 1% by weight of sodium hyaluronate coagulated in 99% concentrated acetic acid. These filaments were slightly drawn.

These filaments are then subject to a tensile stress at a rate of 2 mm/min, the length initially submitted to the load being set to 30 mm. For each type of sample, four tests were conducted.

Young's modulus, yield strength and yield elongation were then determined for each sample, i.e. for each spinning rate.

Figure 3:
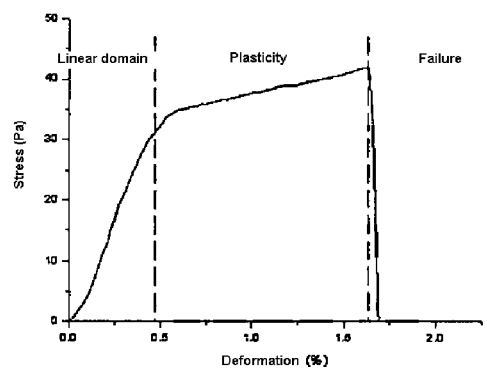
FIG. 3 illustrates the stress/deformation curve obtained after a tensile test at 2 mm/min on a filament according to the invention, not very drawn.

An exemplary tensile curve is given in FIG. 3. It corresponds to the stress/strain curve obtained after a tensile test at 2 mm/min on a not very highly drawn yarn, the spinning rate being 4.7 cm/min. It is observed that after a linear elastic deformation domain, the filament experiences onset of plastic deformation.

4. Crystallinity: X-Ray Diffraction (WAXS)

Figure 4:
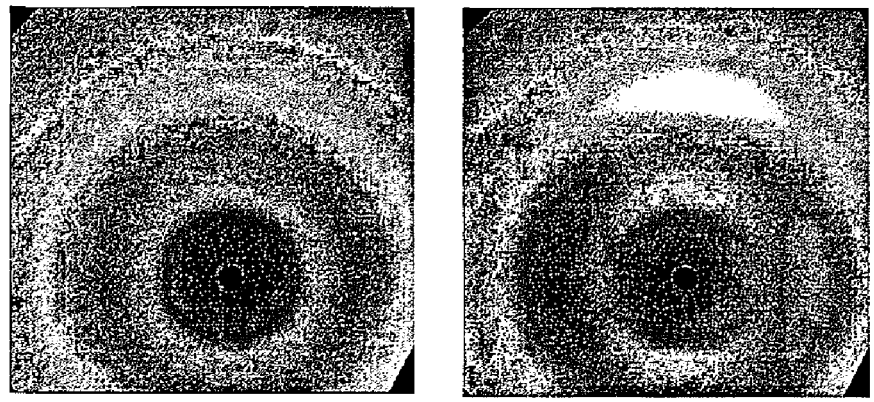
FIG. 4 illustrates the images obtained by X-ray diffraction for a macrofilament: not drawn (FIG. 4a), drawn (FIG. 4b) and highly drawn (FIG. 4c).
Figure 4:
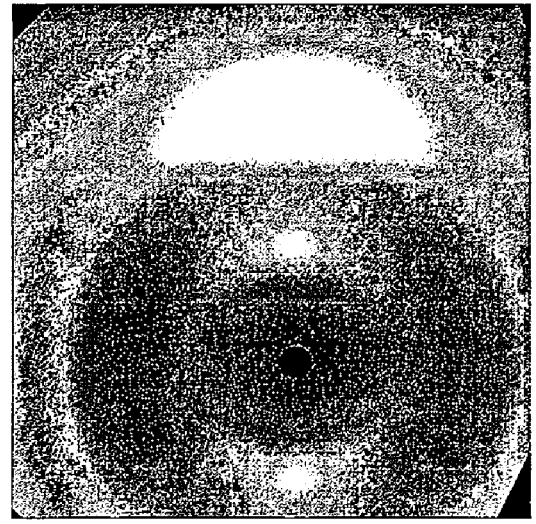

The images obtained by X-ray diffraction are given in FIG. 4 for a hyaluronic acid filament: not drawn (FIG. 4*a*), drawn (FIG. 4*b*) and highly drawn (FIG. 4*c*). These results show the development of crystallinity of the studied samples.

The intensity profile was studied depending on the azimuthal angle with which it was possible to calculate the Hermans orientation function:

$f=-0.02$ of the non-drawn sample (FIG. 4*a*)

and $f=-0.113$ for the highly drawn sample (FIG. 4*c*)

Being aware that:

$-f=-0.5$ for planes perfectly aligned with the axis of the fiber, $-f=1$ for planes perpendicular with the axis of the fiber, and $-f=0$ for isotropically oriented planes, the obtained values show that the crystalline portions of the non-drawn filaments are very slightly oriented in a preferential direction while for the highly drawn sample, the crystalline portions are preferentially oriented along the axis of the filament.

Crystallinity induces within the hyaluronic acid filament a parallel arrangement of nanofibrils, with formation of interfibrillar spaces.

Targeted Applications:

These filaments have particularly interesting properties for the biomedical and surgery fields. A first target application is the filling of wrinkles, because of their capacity of swelling and of the crystalline nature. The more the sample is crystalline, the more its resolubilization, notably at the pHs of biological media such as blood (Ph from 7.2-7.4) of tears (pH of 8) will be slowed down.

Another application aims at the use of a filament based on hyaluronic acid for making textiles, as non-woven fabrics, fabrics or knits, notably in order to form healing bandages.

It is also contemplated to insert active ingredients into the interfibrillar spaces, then transforming the filaments into systems adapted for controlled desalting of active ingredients.

Bibliography:

[1] Dautzenberg H., Jeager W., Philipp B., Seidel C. and Stscherbina D.—Polyelectrolyte: formation, characterisation and application. *Hanser Ed.* (1994)

[2] Meyer, K.; Palmer, J. W.—The polysaccharide of the vitreous humor. *J. Biol. Chem.* (1934), 107, 629.

[3] Weissmann, B.; Meyer, K.—Structure of hyaluronic acid. The glucuronidic linkage. *J. Am. Chem. Soc.* (1952), 74, 4729.

[4] Jeanloz, R.; Flowers, H.—The isolation and synthesis of the methyl estermethyl a-glycoside of 3-O-p-D-glucuronosyl-A/-acetyl-D-glucosamine (hyalobiuronic acid). *J. Am. Chem. Soc.* (1962), 84, 3030.

[5] Balazs, E. A.; Denlinger, J. L.—Viscosupplementation: a new concept in the treatment of osteoarthritis. *J. Rheumatology* (1993), 39, 3-9.

[6] Goa, K.; Benfield, P.—Hyaluronic acid. A review of its pharmacology and use as a surgical id in ophtalmology, and its therapeutic potential in joint disease and wound healing. *Drugs* (1994), 47, 536-566.

[7] Rupprecht, A.—Preparation of oriented DNA by Wet Spinning. *Acta Chemica Scandinavica* (1966), 20, 494-504.

[8] Rupprecht, A.—A wet spinning apparatus and auxiliary equipment suitable for preparing samples of oriented DNA. *Biotechnology and engineering* (1970), 12, 93-121.

[9] Rupprecht, A.—Wet spinning of hyaluronic acid. Preparation of oriented samples. *Acta Chemica Scandinavica* (1979), 33, 779-780.
[10] Um, I. C.; Fang, D. F.; Hsiao, B. S.; et al.—Electro-spinning and electro-blowing of hyaluronic acid. *Biomacromolecules* (2004), 4, 1428-1436.
[11] Wang, X. F.; Um, I. C.; Fang, D. F.; et al.—Formation of water-resistant hyaluronic acid nanofibers by blowing-assisted electro-spinning and nontoxic post treatments. *Polymer* (2005), 46 (13), 4853-4867
[12] Notin L., Viton C., Laurent D., Alcouffe P., Rochas C., Domard A.—Morphology and mechanical properties of chitosan fibers obtained by gel-spinning: Influence of the dry-jet-stretching step and ageing—*Acta biomaterialia* (2006), 387-402

The invention claimed is:

1. A filament based on hyaluronic acid in free acid form obtained by a method comprising:
    preparing a spinnable aqueous solution of hyaluronic acid or of a hyaluronic acid salt;
    extruding said solution through an extrusion die; and
    passing the extruded solution into a solution of acetic acid, the concentration of which is sufficiently high in order to obtain coagulation of the extruded solution as a coagulated filament and is more than 80% by weight, drawing and drying,
    wherein the filament comprises hyaluronic acid, acetic acid and water.

2. A hyaluronic acid filament, obtained by a method comprising:
    preparing a spinnable aqueous solution of hyaluronic acid or of a hyaluronic acid salt;
    extruding said solution through an extrusion die; and
    passing the extruded solution into a solution of acetic acid, the concentration of which is sufficiently high in order to obtain coagulation of the extruded solution as a coagulated filament and is more than 80% by weight, drawing and drying,
    wherein the drying conditions are adjusted so as to totally remove the acetic acid contained in the coagulated filament, and
    wherein the hyaluronic acid filament exclusively contains hyaluronic acid and water.

3. The filament according to claim 1, having a diameter of the order of or greater than 100 μm.

4. A coated filament comprising:
    the filament according to claim 1; and
    a coating comprising at least one compound capable of slowing down hydration of the filament.

5. An inclusion filament comprising the filament according to claim 1, wherein the filament contains at least one active ingredient in its interfibriller spaces.

6. The inclusion filament according to claim 5, wherein the at least one active ingredient is selected from the group consisting of hormones, growth factors, interleukins, interferons, antibacterial agents, antifungal agents, and biostimulating agents.

7. A textile material comprising the filament according to claim 1.

8. A cosmetic for filling wrinkles comprising the filament according to claim 1.

9. A system suitable for controlled desalting of active ingredients comprising the filament according to claim 1.

10. The filament according to claim 1, wherein the concentration of the acetic acid solution is more than 90% by weight.

11. The filament according to claim 1, wherein the preparation of the spinnable solution consists of dissolving in water a determined amount of sodium hyaluronate and of then performing degassing before extrusion.

12. The filament according to claim 1, wherein the spinnable solution has a concentration by weight of hyaluronic acid or of the salt of hyaluronic acid above 0.8%.

13. The filament according to claim 1, wherein the drawing occurs on the coagulated filament with a low drawing ratio of the order of 1.05 to 1.10.

14. The filament according to claim 1, wherein the drawing occurs on the extruded solution before or during the coagulation with a drawing ratio of the order of or greater than 2.

15. The hyaluronic acid filament according to claim 2, wherein the hyaluronic acid filament exclusively contains hyaluronic acid and 8 to 12% by weight water.

16. The coated filament according to claim 4, wherein the at least one compound is selected from the group consisting of chitosan, collagen, and fatty compounds of a vegetable or animal origin.

17. The coated filament according to claim 16, wherein the fatty compounds of a vegetable or animal origin is vegetable wax.

18. The filament according to claim 1, wherein the concentration of the acetic acid solution is more than 90% by weight.

19. The filament according to claim 2, wherein the concentration of the acetic acid solution is more than 90% by weight.

* * * * *